(12) United States Patent
Peeters et al.

(10) Patent No.: US 8,703,442 B2
(45) Date of Patent: Apr. 22, 2014

(54) CONTINUOUS PROCESS FOR SUBSTRATE MODIFICATION USING A PACKED BED COLUMN OF IMMOBILIZED ENZYME

(75) Inventors: Esther Hendrika Gerarda Peeters, Zegge (NL); Marcus Bernardus Kruidenberg, Oostvoorne (NL); Andrew James Dell, Liverpool (GB)

(73) Assignee: Cargill, Incorporated, Wayzata, MN (US)

( * ) Notice: Subject to any disclaimer, the term of this patent is extended or adjusted under 35 U.S.C. 154(b) by 642 days.

(21) Appl. No.: 12/902,241

(22) Filed: Oct. 12, 2010

(65) Prior Publication Data

US 2011/0027828 A1 Feb. 3, 2011

Related U.S. Application Data

(62) Division of application No. 11/729,306, filed on Mar. 28, 2007.

(30) Foreign Application Priority Data

Mar. 31, 2006 (EP) .................................. 06006835

(51) Int. Cl.
*C12P 1/00* (2006.01)
*C12P 7/64* (2006.01)
*C12N 11/00* (2006.01)
*C12N 11/14* (2006.01)
*C12N 11/02* (2006.01)

(52) U.S. Cl.
USPC ............. 435/41; 435/134; 435/174; 435/176; 435/177

(58) Field of Classification Search
None
See application file for complete search history.

(56) References Cited

U.S. PATENT DOCUMENTS

| | | | |
|---|---|---|---|
| 4,029,546 A | 6/1977 | Brouillard | |
| 4,209,591 A | 6/1980 | Hendricks | |
| 4,629,742 A | 12/1986 | Brady et al. | |

FOREIGN PATENT DOCUMENTS

| | | |
|---|---|---|
| DE | 9320595 | 10/1994 |
| EP | 0412467 | 2/1990 |
| WO | 83/03844 | 11/1983 |
| WO | 97/01632 | 1/1997 |

OTHER PUBLICATIONS

X. Xu; "Engineering of enzymatic reaction and reactors for lipid modification and synthesis"; Eur. J. Lipid Sci. Technol. vol. 105, pp. 289-304 (2003).

P. Quinlan & S. Moore; INFORM( International News on Fats, Oils and Related Materials) 4; "Modification of triglycerides by lipases: process technology and its application to the production of nutritionally improved fats", pp. 580-585 (1993).

B.S. Carmail and Y. Kakuda (eds) Improved and Alternative Sources of Lipids; Y.J. Owusu-Ansah "Enzymes in lipid technology and cocoa butter substitutes", pp. 360-389 (1994) by Springer-Science and Business Media, B.V., Dordrecht, Netherlands.

F.D. Gansdone & F.B. Padlee (eds) Lipid Technologies and Applications; A. Rozendaal & A.R. Macrae "Interesterification of Oils and Fats", pp. 223-263 (1997)by Marcel Dekker, Inc., New York, New York.

U.T. Bornscheuer, Enzymes in Lipid Modification; X. Xu; "Modifications of Oils and Fats by Lipase-Catalyzed Interesterification: Aspects of Process Engineering", pp. 190-215 (2000), Wiley-VCH, Weinheim, New York.

C.C. Akoh and D.B. Min (eds), Food Lipids—Chemistry, Nutrition, and Biotechnology; W.M. Willis and A.G. Marangoni; "Enzymatic Interesterification", pp. 839-875 (2002) by Marcel Dekker, Inc., New York, New York.

*Primary Examiner* — David M Naff

(57) ABSTRACT

A process for the modification of a substrate comprising passing the substrate through a packed bed column of a specific volume of immobilized enzyme wherein the substrate enters the column at or near one end of the column (the 'inlet end') and the modified substrate exits at or near the opposite end of the column (the 'outlet end'), a portion of the volume of immobilized enzyme is periodically removed at or near to the inlet end of the column, and an equivalent portion of immobilized enzyme is periodically added at or near to the outlet end of the column.

1 Claim, No Drawings

US 8,703,442 B2

CONTINUOUS PROCESS FOR SUBSTRATE MODIFICATION USING A PACKED BED COLUMN OF IMMOBILIZED ENZYME

CROSS REFERENCE TO RELATED APPLICATIONS

This application is a divisional of co-pending U.S. patent application Ser. No. 11/729,306, filed Mar. 28, 2007, which claims priority to European Patent Application No. 06 006 835.0, filed Mar. 31, 2006, both of which are incorporated herein by reference.

BACKGROUND OF THE INVENTION

1. Field of the Invention

Enzymatic reactions are increasingly used for processing materials on an industrial scale. An important commercial step was the development of immobilized enzymes, i.e., enzymes that are physically attached to a solid support—either by adsorption or chemical bonds—to facilitate the separation of the enzyme from the reaction solution Immobilization also enables multiple or repetitive use of the enzymes and often increases the stability of the enzymes.

2. Description of Related Art

Several types of reactors are used in conjunction with immobilized enzymes: packed bed reactors (also referred to as fixed bed reactors), fluidized bed reactors, stirred batch reactors, continuously stirred tank reactors, and membrane reactors. In large-scale production, packed bed reactors are commonly used for particular applications. In such reactors, the immobilized enzyme is packed in a column or flat bed while substrate and product streams are pumped into and out of the reactor, respectively. The main advantages of this type of reactor are an easy adaptation to larger scales, high efficiency, low costs, ease of operation and also an enhanced surface area per unit volume compared to membrane reactor systems (cf. W. M. Willis and A. G. Marangoni, Enzymatic Interesterification, in: Food Lipids—Chemistry, Nutrition and Biotechnology, edited by C. C. Akok and D. B. Min, pages 839-875).

A type of reaction in which the use of enzymes as catalysts has become increasingly important in recent years in the oils and fats industry is interesterification. Interesterification is the exchange of acyl groups between an ester and an acid (acidolysis), an ester and an alcohol (alcoholysis) or between two esters (transesterification). The enzymes capable of interesterification reactions are lipases such as glycerol ester hydrolases (EC 3.1.1.3). These enzymes are predominantly obtained from bacterial, yeast, and fungal sources. These microorganisms secrete lipases into their environment to digest lipid materials for subsequent uptake. In an aqueous environment, lipases catalyse the hydrolysis of triacylglycerides to produce diacylglycerides, monoacylglycerides, glycerol and free fatty acids. However, under water-limiting conditions, the reverse reaction, the synthesis of esters, can also be achieved. Therefore, the direction of the reaction can be manipulated by regulating the water activity. At very low water concentrations ester synthesis predominates, above a water content of more than a few percent hydrolysis is the prevailing reaction, and in between, usually at a water content of less than 1% (w/v), transesterification is most effective.

Owusu-Ansar described in 1994 the use of immobilized lipases in a stirred tank reactor for the large-scale production of cocoa butter equivalents by lipase-catalysed interesterification (in: B. S. Carmail and Y. Kakuda (eds.) Technological Advances in Improved and Alternative Sources of Lipids, pages 360-389).

A packed bed interesterification process has been disclosed in WO 83/03844 wherein triacylglycerides are dissolved in a polar organic solvent. The lipase was immobilized by precipitation onto kieselguhr, hydroxyapatite or alumina particles.

WO 97/01632 is directed to another process for immobilization of an enzyme, specifically, a lipase or a phospholipase, for the processing of triglyceride oils.

Unilever further disclosed a two-stage process for the production of cocoa butter equivalents and Betapol using packed bed columns (P. Quinlan & S. Moore, Inform 4, 580-585 (1993); A. Rozendaal & A. R. Macrae, in: F D. Gansdone & F B. Padlee (eds.) Lipid Technologies and Applications, 1997, pages 223-263).

X. Xu describes further processes with immobilized lipases, among them a packed bed reactor with a capacity of 10 kg/day (in U. T. Bomscheuer, Enzymes in Lipid Modification, 2000, pages 190-215).

The existing packed bed reactors suffer from the problem of a decrease in conversion rate over time. Though some enzymes such as lipases are quite stable, their efficacy inevitably drops over time, which results in lower reaction rates and non-uniform product quality. This lowering of quality can be counteracted by decreasing the flow rate and thereby increasing the residence time of the reactants in the reactor. Such a reduction in the flow rate, however, leads to a non-uniform output rate and while it can reduce the fluctuations in product quality, it cannot avoid them completely. Furthermore, such a process often uses a number of discrete reactors in series which requires a complex flow control in order to run and maintain the system. The current invention solves these and related problems by using a new type of packed bed column process for enzymatic modification of a substrate.

SUMMARY OF THE INVENTION

The invention relates to a process for the modification of a substrate which comprises passing the substrate through a packed bed column of a specific volume of immobilized enzyme with a flow of substrate in one direction and a periodic exchange of immobilized enzyme in the opposite direction. The substrate enters the column at or near one of its ends (the 'inlet end') and the modified substrate is discharged at or near its other end (the 'outlet end'). A portion of the volume of immobilized enzyme is periodically removed from the inlet end of the column, while an equivalent portion of immobilized enzyme is periodically added at the outlet end, thereby creating a flow of immobilized enzyme in the opposite direction of the substrate flow.

Whenever, in this application, reference is made to "near the inlet end" or "near the outlet end" the term "near" is intended to imply that material (e.g., substrate, modified substrate, immobilised enzyme) is charged to or discharged from the reactor (through an opening, valve or similar) within a reasonable distance from said end, as determined by a skilled person. That could be, for example, 1 to 5%, or 10% of the length of a column measured from the actual end of the column referred to. What is more, expressions such as "at the end" should be understood to include "at or near the end" when used in reference to the column, unless specifically stated otherwise.

DETAILED DESCRIPTION OF THE INVENTION

Hereinafter, the terms "substrate" and "substrate solution" are synonymously used to describe a liquid compound or mixture of compounds or a liquid solution of a compound or of a mixture of compounds, which are meant to react in the presence of the immobilized enzyme. Thereby, a liquid compound or mixture of compounds or a liquid solution of a compound or of a mixture of compounds is produced, which is referred to as "product" or "modified substrate", synonymously.

The invention relates to a process for the enzymatic modification of a substrate by passing the substrate through a packed bed column of immobilized enzyme. The substrate enters the packed bed column at or near one end of the column (hereinafter referred to as the "inlet end") and passes through the column toward its other end (hereinafter referred to as the "outlet end"), where the substrate exits the column.

Preferably, the column is a vertical column with its inlet end at the bottom of the column and its outlet end at the top of the column. In this embodiment, the substrate will enter the bed first at or close to its lowermost portion and leave the column at or close to its uppermost portion.

Advantageously, the substrate and modified substrate-streams can be essentially continuous. This means that, while the substrate and modified substrate streams may be stopped to allow for the periodic change of a portion of the volume of immobilized enzyme, there is no prolonged downtime necessary. This differentiates the present process from existing methods whereby extended periods of downtime were required amongst other things for changing the whole volume of immobilized enzyme. This not only reduces costs per se, but can also prevent cost fluctuations.

According to the present invention, only a defined portion of the immobilized enzyme is periodically removed from the column. This can be achieved, by way of illustration only, with the following procedure. The continuous flow of substrate is stopped. A discharge valve at the inlet end of the column is opened and a defined portion of the slurry containing immobilized enzyme material from the bottom end of the column is released. After a defined amount of this slurry is discharged, the discharge valve is closed and a feeding valve at the outlet end, or in a pipeline feeding toward the outlet end of the reactor is opened, thereby allowing the entry of a fresh slung of immobilized enzyme material into the column from its supply vessel.

The slurry of immobilized enzyme may be formed by adding a defined amount of the modified substrate into the supply vessel. If necessary, to enhance mixing and to improve the wetting of the pores of the immobilized enzyme, the vessel may be equipped with a stirring device, and/or may be operated under vacuum. When a fresh charge of enzyme is to be added to the reactor, the supply vessel can be dc-aerated and the slurry, or a portion thereof, emptied into the column. The feeding valve is then closed allowing the fresh slurry to settle at the end of the packed bed. Finally, the valves regulating the substrate and product streams are reopened.

The reactor may be operated under vacuum. Preferably, however, it will be operated under a certain pressure ("design pressure"). The design pressure should be chosen to allow for a maximum pressure drop over the length of the column. The pressure drop will depend on the characteristics of the immobilized enzyme particles (e.g., particle size distribution), the substrate flow rate and the height of the bed. By way of example only, a suitable design pressure in a relatively high enzyme bed and with a relatively high substrate flow rate might be about 10 Bar. With a lower bed height and slower flow rate, that value might be closer to 6 Bar. The appropriate design pressure for any given reactor will easily be determined by a skilled person.

To ensure that the design pressure is not exceeded by the feed pressure, the feeding pumps should not have a capacity above the design pressure. What's more, the reactor inlets should be equipped with non-return valves, open/close valves and flow-rate control devices.

Ideally, the discharge of spent enzyme and addition of fresh enzyme will occur concurrently or substantially concurrently. By this, it is meant that the discharge and addition should be performed during the same downtime. It is also preferred that substantially the same quantity of enzyme material is discharged as is added, thereby ensuring that the reactor maintains its packed bed characteristics. Exception to both these rules may occur, for instance, after initial start-up of the reactor, owing to a certain amount of compaction in the column. It may indeed be necessary, in this situation, to add a little more slurry than is discharged or even to add slurry without any discharge.

By repeating this change of a portion of the bed material, a gradual flow of the immobilized enzyme from the top to the bottom of the column is assured. In consequence, the substrate solution will first come in contact with the most exhausted enzyme material and lastly with the freshest enzyme.

Advantageously, the periodic change of a portion of the immobilized enzyme can be largely automated, thereby limiting operator involvement, reducing associated costs, and restricting the probability of any malfunctions.

This system can be compared with multiple separate small basic reactors in series. In comparison to such a series, the complexity of the present invention is greatly reduced, particularly the number of input and output valves. Moreover, the processed solution will not have to be transported between the multiple reactors. This is particularly important when the substrate and/or product solution has to be kept at a certain temperature, or when they have a high viscosity. In addition, a system of small reactors requires that one or more of the reactors is periodically out of service while spent enzyme is removed and fresh enzyme added. This is an intensive manual operation and, during this time, the efficiency of the entire system is greatly reduced. Accordingly, the overall capital and operating costs for such a system are not optimal. What is more, the system of the present invention will allow for an almost infinite gradation of enzyme activity from fresh enzyme to spent enzyme. This could not be achieved even with a great number of separate reactors.

The process of the invention allows for an essentially continuous flow rate, as basically all substrate encounters the same amount of enzyme activity during its passage through the reactor. As the activity of the immobilized enzyme varies with age and use, the uniform contact of substrate with enzyme at various stages of activity is decisive to ensure a more constant product quality. Therefore, a constant flow rate can be applied.

The frequency with which enzyme material is replaced will depend, amongst other things, on the rate of activity decrease of the enzyme over time and the desired residence time of the substrate solution in the packed enzyme bed. The volume of enzyme material changed and the length of the intervals between these changes can easily be adapted to the needs of the process and/or substrate. In addition, there will be a relation between the frequency with which the enzyme is refreshed and the volume of enzyme that is refreshed. With all other process variables remaining constant, a small amount of enzyme can be refreshed frequently or a larger amount of enzyme refreshed less frequently. Preferably, a fixed percentage of the entire column volume will be refreshed on a daily basis. Ideally, that percentage will be less than 35% of the total volume of immobilized enzyme. Preferably, it will be less than 25%, more preferably less than 10%, even more preferably less than 5%. According to one possible embodiment, between about 0.3% and about 3% of the total volume of immobilized enzyme will be refreshed on a daily basis.

After passing through the packed bed column of immobilized enzyme, a sufficient conversion of the substrate should be reached. At the top of the column, product outlet may be facilitated by small cylindrically shaped filter screens. These regulate the outflow of the product while the immobilized enzyme material is kept inside the reactor. There are two types of screens: vent screens and standard screens. While the standard screens are used for the actual outflow of product, the vent screens are higher up in the column and facilitate the flow of air or gas during draining and refilling.

The pumps regulating the input and output of the enzyme material slurries should be designed so that they do not break up the immobilized enzyme creating additional fines. This will assist an even flow and prevent fines from passing subsequent filtering devices.

The discharged enzyme will be a slurry of used (or "spent") immobilized enzyme and substrate solution. This slurry can be separated and the substrate solution can be re-introduced into the tank, which provides the input of substrate to the reaction column. The used enzyme can be disposed of. Preferably, however, it will be processed for further use.

The enzyme removed from the column can indeed be subject to recycling. For instance, in some cases the enzyme removed from the column still has some residual activity, which may be accessed if the immobilized material is broken into smaller particles, thereby revealing active sites of the enzyme that were previously not at all or just restrictedly accessible to the substrate (this is known as "reactivation"). Alternatively, the enzyme may be regenerated and reused. Thus, in a preferred embodiment of the process according to the invention, the enzyme material discharged from the column is regenerated or reactivated and reused, e.g., for pre-treating the substrate prior to it entering the column, or by being added to the tank which supplies the input of immobilized enzyme. It may also be re-used in other systems like batch-modification.

The process of the present invention may be operated in a single column or by passing the substrate through two or more columns of immobilized enzyme disposed in parallel. The term "immobilized enzyme" takes its normal meaning in the art, i.e., that of an enzyme which is physically attached to a solid support. Preferred supports include silica and resin supports. The immobilized enzyme may be present in the form of granules, agglomerated particles or any other form deemed suitable by a skilled person.

The choice of enzyme will, of course, depend on the type of reaction to be carried out, i.e., on the nature of the substrate and its desired modification. It could be any oxidoreductase, transferase, hydrolase, lysase, isomerase or ligase available in the art. By way of illustration, suitable hydrolases could include carboxylic ester hydrolases (EC-3.1.1), such as carboxylesterases, triacylglycerol lipases, phospholipase A2, sterol esterases, acylglycerol lipases, phospholipase A1, and wax-ester hydrolases; and phosphoric diester hydrolases (EC-3.1.4), such as phospholipase C and phospholipase D. These enzymes can be used, for example, to catalyse hydrolysis, alcoholysis or the corresponding reverse conversion (condensation). Other suitable enzymes will be known to the skilled person depending on the specific modification to be performed.

The substrate will be any material or substance capable of being acted upon by an enzyme. It may include, for instance, one or more lipids, one or more proteins, one or more carbohydrates or a mixture thereof. The term "lipid", as used herein, refers not only to crude or processed oils and fractions thereof; but also to triacylglycerides, diacylglycerides, monoacylglycerides, phospholipids, free fatty acids, fatty acid esters and mixtures thereof. The term "protein" may refer, amongst others, to both complex and simple polypeptides, whether in their folded or denatured state, to short peptide sequences and to single amino-acids. The term "carbohydrate" refers, for instance, to single monosaccharide units, disaccharides, oligosaccharides and polysaccharides, such as starch, cellulose and so on. The substrate may be mixed with other reagents (such as an alcohol or water), or with a solvent if necessary. If desired, the substrate may be refined before entering the column. Refining refers to the removal of impurities such as residues and by-products and will contribute to extending the life of the immobilized enzymes.

As stated above, the process of the present invention may be used to perform any type of enzymatic reaction. Nonetheless, a number of possible embodiments will now be described in further detail by way of illustration. These should not be interpreted in any way as limiting the scope of the invention. Rather, their teachings should be understood, where appropriate, to apply to the invention as a whole.

Interesterification

This embodiment concerns the interesterification of oils. Interesterification changes the acyl-glycerol profile of the oil or oil mixture, thereby modifying its physical properties.

According to this embodiment, the enzyme of choice is a lipase. It will ideally be immobilized on a silica support. A suitable immobilized enzyme is the Lypozyme TL IM lipase from Novozymes.

The substrate, which may be used in a refined or unrefined state depending on requirements, will typically comprise an acylglyceride such as a triacylglyceride, a diacylglyceride, a monoacylglyceride or a mixture of two or more thereof. It may be derived from a plant, animal, fish, algae or single-cell source. Preferably, it will be derived from a plant source. Suitable substrates will therefore include, but are not limited to, palm kernel oil, palm oil, coconut oil, olive oil, rapeseed oil, canola oil, linseed oil, ground nut oil, soybean oil, cotton seed oil, sunflower seed oil, pumpkin seed oil, corn oil, castor oil, walnut oil and mixtures of two or more thereof. The substrate may include whole oils and/or oil fractions such as stearins or oleins.

According to one embodiment, the substrate will comprise palm stearin, coconut oil, palm kernel oil or a mixture of two or more thereof. Preferably, the substrate will comprise a mixture of palm stearin plus coconut oil or a mixture of palm stearin plus palm kernel oil. Even more preferably, the mixture will include 50-80% by weight palm stearin and 50-20% by weight coconut oil and/or palm kernel oil, based on total substrate weight. Ideally, the mixture will include 65-75% by weight palm stearin and 35-25% by weight coconut oil or 60-70% by weight palm stearin and 40-30% by weight palm kernel oil. According to a most preferred embodiment, the substrate of the present invention will consist of such a mixture.

The substrate will be pumped through one or more columns in parallel filled with the immobilized enzyme. The substrate and immobilized enzyme material will flow in opposite directions with the oil input at or near the bottom of the column and the fresh enzyme material being added at or near the top. Periodically, a part of the immobilized enzyme will be exchanged with fresh enzyme material. Therefore, the enzyme in the column will have a nearly constant quality profile. The immobilized enzyme a the top of the column will be most fresh with nearly fill activity and the immobilized enzyme near the bottom of the column will be nearly exhausted of activity. Accordingly, there will be a gradation of activity along the length of the column.

The interesterification reaction should be carried out at a defined temperature. This temperature will be chosen with a number of factors in mind.

- as most of the interesterified oils and fats produced according to this process are intended for nutritional products, the process will preferably be free of organic solvents. As such, the process should be performed at a temperature which guarantees that the oils/fats remain in a liquid state;
- the temperature should be high enough to allow a high reaction rate which, in turn, will allow for shorter residence times;
- the temperature should be low enough to not affect the stability and activity of the enzyme. Microbial lipases are quite thermostable and immobilization was found to further improve the stability of these enzymes so that the optimal temperatures for many lipases range from 30° C. to 62° C. (W. M. Willis and A. G. Marangoni, in Enzymatic Interesterification, Food Lipids-Chemistry, Nutrition, and Biotechnology, edited by C. C. Akoh and D. B. Min). Some lipases even allow temperatures of 60° C. to 75° C. (WO 97/01632). Future enzyme development could include even more temperature resistant varieties, e.g., resistant to 80° C., 90° C., 100° C. or above. At these temperatures, most triacylglycerides, even fully saturated ones, will be in a liquid state.

Taking these factors into account, the skilled person will be able to determine the ideal reaction temperature.

By way of example, interesterification of palm stearin with coconut oil by Lypozyme TL IM (Novozymes) will preferably be performed at about 70° C.

After heating the oils to the desired temperature and mixing, if necessary, they are directed to the input valve at or near the inlet end of the reactor. The reactor will preferably be designed to operate under vacuum and up to a suitable pressure.

Fresh immobilized enzyme is supplied at the top of the column at regular intervals. A defined amount of interesterified product oil may be pumped into the supply vessel and mixed with the immobilized enzyme to produce a free-flowing slurry. To enhance mixing and to improve the wetting of the pores of the immobilized enzyme, a vacuum can be applied to the vessel. Advantageously, the vessel will be flushed with nitrogen to prevent oxidation of the oil.

When a fresh charge of enzyme is to be added to the column, the supply vessel is de-aerated, if applicable, and the slurry, or a portion thereof, emptied into the reactor. If required, the vessel and pipelines can be flushed with a certain volume of product oil to ensure complete emptying of the vessel. Preferably, the supply vessel will be situated above the reactor to facilitate enzyme loading.

The process of this embodiment will preferably be essentially continuous. The only downtime will be the few moments that it takes to exchange a portion of the enzyme from the column. This downtime is only a very small fraction of the overall running time of the process.

Alcoholysis

Unless otherwise stated, the details of this embodiment are the same as for the interesterification reaction described above.

The substrate will be a suitably agitated mixture of one or more oils and one or more alcohols. Suitable alcohols include, but are not limited to, methanol, ethanol, glycerol, monopropylene glycol, ethylene glycol, butane diol, erythritol, pentaerythritol, sorbitol, sterols, stanols, tocopherols, polyphenols, esters of such alcohols and mixtures of two or more thereof. The immobilized enzyme will preferably be lipase.

The reaction will preferably be carried out at 50-70° C. After being collected at the outlet of the reactor, the products (fatty acid esters and glycerol) can be isolated. Isolation can be performed by cooling to a temperature where phase separation occurs followed by isolation of the fatty acid ester phase and a drying step. The alcohol can be recovered by evaporation directly from the mixture or after isolating the fatty acid esters.

Glycerolysis

Glycerolysis is a specific type of alcoholysis, as described above. The substrate is a mixture of one or more oils and glycerol. The enzyme is a lipase immobilized on a carrier which is inert against glycerol.

The substrate is prepared by mixing or dissolving glycerol into the oil(s) at reaction temperature or slightly above. The amount of glycerol mixed with the oil can he increased by adding an emulsifier. Depending on the glycerol-to-oil ratio, the enzyme closest to the inlet end of the reactor will act both as a substrate purifier and to adjust the equilibrium concentration of glycerol in the substrate.

The reaction will preferably be carried out at 50-70° C. The product recovered after modification will depend on the glycerol-to-oil ratio of the substrate.

Hydrolysis

In this embodiment, which follows the interesterification embodiment described above, unless indicated to the contrary, the substrate is a pumpable lecithin or lecithin solution. A lecithin solution may be obtained by mixing lecithin with a solvent such as hexane and water.

The enzyme will be a lipase or phospholipase. Depending on the enzyme, different products will be obtained. Thus, if a lipase is used, the product will be a mixture of phospholipids and mono- and/or diglycerides. Using phospholipase A or B, at a preferred reaction temperature of 20-70° C., will lead to the production of lysophospholipids. Using phospholipase C, at a preferred reaction temperature of 20-50° C., will lead to the production of di- and/or triglycerides. Using phospholipase D, at a preferred reaction temperature of 20-70° C., will lead to the production of phosphatidic acid. If necessary, a mixture of different enzymes can be used to obtain the desired product.

After conversion, the product mixtures can be used as such or after further purification steps (e.g., washing, drying, evaporation, fractionation, etc.).

Isomerisation

Another possible reaction which could be performed according to the process of the present invention is isomerisation. A typical example of isomerisation is the conversion of glucose to fructose. Thus, according to one embodiment, the substrate will preferably be glucose (or a glucose syrup) and the immobilized enzyme will preferably be a glucose isomerase (EC 5.3.1.5). The reaction should ideally be carried out between 55-75° C. The product will be a syrup containing both glucose and fructose. If desired, the fructose content can be further increased by purification or by splitting the glucose and fructose into separate products.

The invention claimed is:

1. A continuous process for modification of a substrate comprising the following steps:

a) providing a packed bed column of immobilized enzyme, said column being substantially vertical with an inlet end at the bottom of the column and an outlet end at the top of the column;
b) continuously adding a substrate to the column at the inlet end;
c) continuously passing the substrate upward in the column through the packed bed to enzymatically modify the substrate by the immobilized enzyme to produce a modified substrate;
d) continuously discharging modified substrate from the column at the outlet end;
e) periodically removing a portion of the immobilized enzyme from the column at the inlet end while performing steps b)-d), wherein the portion of immobilized enzyme removed is less than 35% of total immobilized enzyme volume in the column;
f) periodically adding a portion of immobilized enzyme to the column at the outlet end while performing steps b)-d), wherein the portion of immobilized enzyme added is substantially equivalent in volume to the portion of immobilized enzyme removed, and wherein adding immobilized enzyme to the column and removing immobilized enzyme from the column occur substantially concurrently; and
g) using the portion of immobilized enzyme removed from the column to pre-treat the substrate before the substrate enters the column.

* * * * *